United States Patent [19]
Laneman et al.

[11] Patent Number: 5,902,904
[45] Date of Patent: May 11, 1999

[54] METHOD FOR PREPARATION OF TERTIARY PHOSPHINES VIA NICKEL-CATALYZED CROSS COUPLING

[75] Inventors: Scott A. Laneman, Vernon Hills; David J. Ager, Hoffman Estate, both of Ill.; Amihia Eisenstadt, Ramat-Hasharon, Israel

[73] Assignee: Monsanto Company, St. Louis, Mo.

[21] Appl. No.: 09/138,004

[22] Filed: Aug. 21, 1998

Related U.S. Application Data

[63] Continuation of application No. 08/824,309, Mar. 26, 1997.

[51] Int. Cl.$^6$ ........................................ C07F 9/50
[52] U.S. Cl. ................... 568/8; 568/10; 568/17; 564/15
[58] Field of Search ..................... 568/8, 10, 16, 568/17; 564/15

[56] References Cited

U.S. PATENT DOCUMENTS

| | | |
|---|---|---|
| 3,470,254 | 9/1969 | Hechenbleikner . |
| 3,723,536 | 3/1973 | Stuebinger . |
| 4,036,889 | 7/1977 | Chopdekar . |
| 4,045,494 | 8/1977 | Chopdekar . |
| 4,356,324 | 10/1982 | Bergstein ................................. 568/17 |
| 4,668,823 | 5/1987 | Murray ...................................... 568/17 |
| 4,758,315 | 7/1988 | Folest et al. ........................... 204/59 R |
| 4,956,055 | 9/1990 | Puckette . |
| 5,028,576 | 7/1991 | Drent ....................................... 502/162 |
| 5,268,492 | 12/1993 | Yamamoto ............................... 549/460 |
| 5,284,977 | 2/1994 | Imori ........................................... 568/8 |
| 5,399,771 | 3/1995 | Cai ............................................ 568/17 |
| 5,516,944 | 5/1996 | Broger ...................................... 568/13 |
| 5,527,967 | 6/1996 | Millauer ................................... 568/17 |
| 5,621,129 | 4/1997 | Hayashi .................................... 556/21 |
| 5,654,486 | 8/1997 | Senaratine ................................ 568/17 |
| 5,710,337 | 1/1998 | Unruh ....................................... 568/16 |

FOREIGN PATENT DOCUMENTS

| | | | |
|---|---|---|---|
| 0 268 526 | 5/1988 | European Pat. Off. .......... | C25B 3/04 |
| 0 732 336 | 9/1996 | European Pat. Off. .......... | C07F 9/53 |

OTHER PUBLICATIONS

S. E. Tunney and J. K. Stille, Journal of Organic Chemistry, 52 748–53 (1987) "Palladium–Catalyzed Coupling of Aryl Halides with (Trimethylstannyl)diphenylphosphine and (Trimethylsilyl)diphenylphosphine".

CA:108:167657, abstract of "Enantioselective Catalysis", Bronner, Bull. Soc. Chim. Belg., 9665) pp. 353–359.

D. Ager, et al., "Convenient and Direct Preparation of Tertiary Phosphines via Nickel–catalysed Cross–Coupling", Chem. Commun., 1997, pp. 2359–2360.

*Primary Examiner*—Gary Geist
*Assistant Examiner*—Jean F Vollano
*Attorney, Agent, or Firm*—Fitzpatrick, Cella, Harper & Scinto

[57] ABSTRACT

The invention is an improved method for the preparation of tertiary phosphines by way of cross-coupling of aryl, alkenyl, cycloalkenyl or aralkyl halides or aryl, alkenyl, cycloalkenyl or aralkyl sulfonate esters with chlorophosphines in the presence of a catalyst and a reductant. The general reaction scheme is shown below:

$$R^1X_n + ClPR^2R^3 \xrightarrow[\text{reductant}]{\text{catalyst}} R^1(PR^2R^3)_n$$

wherein $R^1$ is aryl, alkenyl, cycloalkenyl or aralkyl, any of which may be substituted by one or more of the following: alkyl, aryl, aralkyl, alkoxy, alkanoyl, chloro, fluoro, alkoxycarbonyl, cyano, trifluoromethyl, cycloalkyl, or $CONR^4R^5$ wherein $R^4$ and $R^5$ are independently hydrogen, alkyl, aryl or aralkyl; $R^2$ and $R^3$ are independently aryl, alkyl, aralkyl, any of which may be substituted by one or more of the following: alkyl, aryl, aralkyl, alkoxy, alkanoyl, chloro, fluoro, alkoxycarbonyl, cyano, trifluoromethyl, cycloalkyl or $CONR^4R^5$ wherein $R^4$ and $R^5$ are independently hydrogen, alkyl, aryl or aralkyl; and n is 2 where $R^1$ is a difunctional moiety and 1 for any other $R^1$; and X is Cl, Br, I, or $OSO_2Y$; wherein Y is alkyl, trihalomethyl, phenyl, halophenyl, or alkylphenyl.

11 Claims, No Drawings

METHOD FOR PREPARATION OF TERTIARY PHOSPHINES VIA NICKEL-CATALYZED CROSS COUPLING

This application is a continuation of U.S. patent application Ser. No. 08/824,309, filed Mar. 26, 1997, now pending.

BACKGROUND OF THE INVENTION

1. Field of the Invention

The invention relates to an improved method for the preparation of tertiary phosphines by cross-coupling of aryl, alkenyl, cycloalkenyl or aralkyl halides, or aryl, alkenyl, cycloalkenyl or aralkyl sulfonate esters, with chlorophosphines in the presence of a catalyst and a reductant.

2. Related Background Art

Tertiary phosphines, especially triarylphosphines, are well known as ligands for transition metal catalysts. Preparation of tertiary phosphines typically proceeds by one of four methods: reaction of halophosphines with aryl Grignard reagents or organolithium reagents, metalation of diarylphosphines followed by reaction with aryl halides or aryl sulfonate esters, Friedel-Crafts reactions of halophosphines with activated aromatic rings, and cross-coupling of aryl halides or aryl triflates with diarylphosphines.

Reactions of aryl Grignard reagents or organolithium reagents with halophosphines are limited to cases in which there are no functional groups present on the aryl moieties which react with the Grignard reagents, such as halo, alkanoyl, or ester substituents. In addition, this method requires special handling procedures for the moisture-sensitive and relatively unstable Grignard reagents or organolithium reagents.

Preparation of tertiary phosphines by metalation of diarylphosphines also requires handling of Grignard or organolithium reagents, with the accompanying problems mentioned above, as well as special procedures necessitated by the fact that diarylphosphines are light-sensitive and pyrophoric. Another disadvantage of this method is that metalated diarylphosphines are extremely nucleophilic and will react with certain functional groups on the aryl moieties of the starting materials, such as halo and alkoxy substituents.

Friedel-Crafts reactions are disadvantageous because they typically employ extremely acidic catalysts such as aluminum bromide, aluminum chloride, ferric chloride, or sulfuric acid. Such catalysts may be incompatible with a variety of functional groups on the aryl moieties. In addition, these catalysts are corrosive and moisture-sensitive, and thus difficult to handle.

As previously mentioned, cross-coupling of aryl halides or triflates with diarylphosphines to produce triarylphosphines is also known.

Tunney and Stille, Journal of Organic Chemistry, Vol. 52, page 748 (1987), prepared triarylphosphines by carrying out a palladium-catalyzed cross-coupling of aryl halides and either (trimethylsilyl)diphenylphosphine or (trimethylstannyl)diphenylphosphine. The major disadvantage of this method is that (trimethylsilyl)diphenylphosphine and (trimethylstannyl)diphenylphosphine are pyrophoric, and thus require special handling procedures. An additional disadvantage is that these reagents are expensive. A limitation of the method of Tunney and Stille is that the trimethylsilyl-substituted starting material, preferred due to the much greater toxicity of the trimethylstannyl compounds, reacts with hydroxyl, amino, nitro, and aldehyde groups on the aryl moieties, preventing application of the method to preparation of triarylphosphines bearing these functional groups. Another limitation is that only aryl halides are used as starting materials, and not arylsulfonate esters. Yet another limitation is that only triarylphosphines are produced by this method because only aryl halides are used as starting materials. There is no suggestion of using benzyl halides as starting materials to make benzylarylphosphines.

A cross-coupling reaction to prepare triarylphosphines is also described in U.S. Pat. No. 5,399,771, which discloses the use of a nickel-catalyzed cross-coupling reaction of a 1,1'-bi-2-naphthol disulfonate ester with diphenylphosphine to produce 2,2'-bis(diphenylphosphino)-1,1'-binaphthyl. This reference exemplifies only the specific transformation mentioned above, and limits the disulfonate ester starting material to the triflate, mesylate or tosylate; no suggestion is made of the possibility of using a halide starting material. A disadvantage of this method is that one of the starting materials, i.e., diphenylphosphine, is light-sensitive and pyrophoric, thus requiring special handling.

The use of diarylchlorophosphines as reagents in the catalytic preparation of tertiary phosphines is neither suggested nor exemplified by the aforementioned references.

A method for production of tertiary phosphines in which the starting materials are inexpensive and easily handled, and which is adaptable to using either aryl or benzyl starting materials containing either halo or sulfonate ester substituents, would be highly advantageous.

SUMMARY OF THE INVENTION

A method is provided for preparation of a compound of formula $$R^1 \, (PR^2R^3)_n$$

wherein $R^1$ is aryl, alkenyl, cycloalkenyl or aralkyl, any of which may be substituted by one or more of the following: alkyl, aryl, alkoxy, alkanoyl, chloro, fluoro, alkoxycarbonyl, cyano, trifluoromethyl, cycloalkyl, or $CONR^4R^5$ wherein $R^4$ and $R^5$ are independently hydrogen, alkyl, aryl or aralkyl; $R^2$ and $R^3$ are independently aryl, alkyl, or aralkyl, any of which may be substituted by one or more of the following: alkyl, aryl, aralkyl, alkoxy, alkanoyl, chloro, fluoro, alkoxycarbonyl, cyano, trifluoromethyl, cycloalkyl or $CONR^4R^5$ wherein $R^4$ and $R^5$ are independently hydrogen, alkyl, aryl or aralkyl; n is 2 where $R^1$ is a difunctional moiety, such as 1,1'-binaphth-2,2'-diyl, phenylene, or xylylene, and n is 1 in all other cases. The method comprises the step of treating a compound of formula $R^1X_n$; wherein X is Cl, Br, I, or $OSO_2Y$; wherein Y is alkyl, trihalomethyl, phenyl, halophenyl, or alkylphenyl; with a compound of formula $R^2R^3PCl$, a catalyst, and a reductant.

DETAILED DESCRIPTION OF THE INVENTION

The following abbreviations and terminology are used herein. The term "alkyl" refers to a straight-chain or branched alkyl group having 1–30 carbon atoms which may be unsubstituted or substituted by fluoro, chloro, alkoxy, alkanoyl, cyano, alkoxycarbonyl, or cycloalkyl. The term "cycloalkyl" refers to a cyclic alkyl substituent having 3–20 carbon atoms. The term "alkenyl" refers to a straight-chain or branched group having 1–30 carbon atoms with at least one carbon-carbon double bond and which may be unsubstituted or substituted by fluoro, chloro, alkoxy, alkanoyl, cyano, alkoxycarbonyl, or cycloalkyl. The term "cycloalkenyl" refers to a cyclic alkenyl group having up to 20 carbon atoms. The term "alkoxy" refers to a substituent containing an alkyl group attached to, and bonded through an oxygen atom. The term "halo" refers to a substituent derived from fluorine, chlorine, bromine, or iodine. The term "aryl" refers to a substituent derived from any cyclic aromatic compound having 5–20 carbon atoms. The term "aralkyl" refers to an alkyl substituent substituted by an aryl group. The term "Ph" refers to a phenyl substituent. The term "dppe" refers to 1,2-bis-(diphenylphosphino)ethane. The term "triflate" refers to the trifluoromethanesulfonyl ester. The term "BINAP" refers to 2,2'-bis(diphenylphosphino)-1,1'-binaphthyl. The term "1,1'-binaphth-2,2'-diyl" refers to the divalent substituent moiety having the structure shown below.

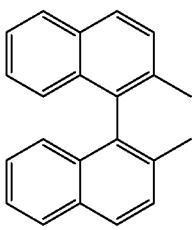

In a preferred embodiment of this invention, an aryl, alkenyl, cycloalkenyl or aralkyl moiety substituted by a sulfonate ester or a halo substituent is reacted with a diarylchlorophosphine in the presence of a nickel catalyst and zinc, as shown in the following scheme:

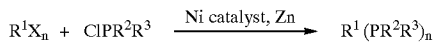

If $R^1$ is aryl, the preferred moieties are phenyl, pyridyl, furyl, thienyl, pyrrolyl, naphthyl, 1,1'-binaphth-2,2'-diyl and its stereoisomers, or phenylene. The 1,1'-binaphth-2,2'-diyl and phenylene moieties are difunctional, and in these cases, n will be 2 in both the reactant and product in the above scheme. The other aryl moieties listed above are monofunctional, and thus n will be 1 for these. Any of the above aryl moieties may be substituted by one or more of the following: alkyl, aryl, aralkyl, alkoxy, alkanoyl, chloro, fluoro, alkoxycarbonyl, cyano, trifluoromethyl, cycloalkyl, or $CONR^4R^5$ wherein $R^4$ and $R^5$ are independently hydrogen, alkyl, aryl or aralkyl.

If $R^1$ is aralkyl, the preferred moieties are benzyl, pyridylmethyl, furfuryl, thienylmethyl, pyrrolylmethyl, naphthylmethyl, or xylylene. The xylylene moiety is difunctional, and in this case, n will be 2 in both the reactant and product in the above scheme. The other arylmethyl moieties listed above are monofunctional, and thus n will be 1 for these. Any of the above arylmethyl moieties may be substituted by one or more of the following: alkyl, aryl, aralkyl, alkoxy, alkanoyl, chloro, fluoro, alkoxycarbonyl, cyano, trifluoromethyl, cycloalkyl, or $CONR^4R^5$ wherein $R^4$ and $R^5$ are independently hydrogen, alkyl, aryl or aralkyl.

The reactive group attached to the $R^1$ moiety, represented by X in the scheme shown above, may be either a sulfonate ester or a halide. A sulfonate ester substituent on an aryl or aralkyl moiety may be, for example, alkylsulfonyloxy, trihalomethylsulfonyloxy, arylsulfonyloxy, haloarylsulfonyloxy, aralkylsulfonyloxy, or alkarylsulfonyloxy. The most preferred sulfonate ester substituent for carrying out the method of this invention is trifluoromethylsulfonyloxy, also known as triflate. X may also be a halo substituent. The most preferred halo substituent is bromo.

$R^2$ and $R^3$ may be independently alkyl, aryl, or aralkyl, any of which may be substituted by one or more of the following: alkyl, aryl, aralkyl, alkoxy, alkanoyl, chloro, fluoro, alkoxycarbonyl, cyano, trifluoromethyl, cycloalkyl, or $CONR^4R^5$ wherein $R^4$ and $R^5$ are independently hydrogen, alkyl, aryl or aralkyl. Preferably, $R^2$ and $R^3$ are independently phenyl, alkyl, furyl, thienyl, pyrrolyl, pyridyl, benzyl, or naphthyl, any of which may be substituted by one or more of the following: alkyl, aryl, aralkyl, alkoxy, alkanoyl, chloro, fluoro, alkoxycarbonyl, cyano, trifluoromethyl, cycloalkyl, or $CONR^4R^5$ wherein $R^4$ and $R^5$ are independently hydrogen, alkyl, aryl or aralkyl.

The catalyst employed in this invention may be a nickel catalyst. Preferred nickel catalysts may be, for example, $NiCl_2$, $NiBr_2$, or $NiZ_2L_m$ wherein Z is chloro or bromo and either L is $(R^6)_3P$ and m is 2, or L is $(R^6)_2P(CH_2)_kP(R^6)_2$ and m is 1; wherein $R^6$ is phenyl, phenyl substituted by one or more alkyl or alkoxycarbonyl substituents, alkyl, or cycloalkyl, and k is an integer between one and six, inclusive. The most preferred catalyst is $NiCl_2[Ph_2P(CH_2)_2PPh_2]$, otherwise referred to as $NiCl_2$ (dppe).

A reductant is necessary to activate the chlorophosphine starting material, facilitating the catalyzed cross-coupling to produce the tertiary phosphine directly. Preferably, zinc may be used as a reductant in combination with a nickel catalyst. Most preferably, the zinc is preactivated by washing with hydrochloric acid, rinsing with water, and then drying. It is preferred to add the zinc to a mixture of the reactants and a solvent, maintaining the temperature between 5 and 15° during the addition.

Suitable solvents for the reaction carried out in this invention include the polar aprotic solvents, such as, for example, N,N-dimethylformamide (DMF), N,N-dimethylacetamide, N-methylpyrrolidone, and tetrahydrofuran. The most preferred solvent for carrying out the method of this invention is N,N-dimethylformamide. However, any solvent may be employed which allows for the preparation of tertiary phosphines using the method of this invention.

The reaction proceeds when the reactants are heated in the presence of the catalyst and the reductant. The reaction mixture is generally heated to a temperature in the range from about 60 to about 150° C., preferably from about 80 to about 120° C. The temperature is typically maintained within these ranges until the reaction is substantially complete as determined, for example, by the analysis of the reaction mixture by a technique such as gas chromatography to determine when the starting materials have been depleted or when their levels are no longer decreasing. The reaction times may vary from about one hour to about 19 hours.

One advantage of the method of this invention over the two known methods utilizing a cross-coupling reaction for production of tertiary phosphines is that aryl and aralkyl moieties bearing a halide substituent as well as those bearing a sulfonate ester substituent are suitable starting materials for the coupling reaction of this invention. Each of the previous methods utilized either starting materials bearing a halide substituent or starting materials bearing a sulfonate ester substituent. Neither of these methods features both sulfonates and halides as potential starting materials.

Another advantage of the method of this invention is that the diarylchlorophosphine starting materials, especially $Ph_2PCl$, are readily available, inexpensive, and are not pyrophoric as are diphenylphosphine, (trimethylstannyl)diphenylphosphine and (trimethylsilyl)diphenylphosphine.

The examples which follow are intended as an illustration of certain preferred embodiments of the invention, and no limitation of the invention is implied.

EXAMPLE 1

Preparation of BINAP from 1,1'-Binaphth-2,2'-diyl ditriflate

To a solution of 8.25 g (30 mmol) of 1,1'-binaphth-2,2'-diyl ditriflate in 40 ml DMF, was added all at once 5.4 ml $ClPPh_2$ (30 mmol) and 500 mg $NiCl_2(dppe)$ (0.95 mmol). Zinc powder (2.31 g, 36 mmol) was added portionwise to the reaction mixture with vigorous mechanical stirring while the mixture was cooled externally in an ice-water bath. The mixture was then heated with stirring at 100° C. for 19 hours. Then, the mixture was cooled to room temperature, filtered and washed twice with 10 ml methanol. The isolated solid (5 g) had a purity of 96–97%, as determined by gas chromatographic analysis. Further purification was conducted by continuous extraction with methylene chloride in a soxhlet apparatus; substantially pure product was extracted, leaving zinc salts behind in the residue. The overall yield of BINAP was 52%.

EXAMPLE 2

Preparation of Methyl 2-(diphenylphosphino)benzoate

To a solution of 17.08 g (58 mmol) of methyl 2-(trifluoromethylsulfonyloxy)benzoate in 95 ml DMF, were added 1.163 g $NiCl_2(dppe)$ (2.2 mmol) and 10.8 ml $ClPPh_2$ (60 mmol). The reaction mixture was cooled in ice-water bath, and 5.3 g zinc (83 mmol) was added portionwise at 8–15° C. The reaction mixture was heated to 108° C. for 4 hours, then filtered while at 80° C. One third of the filtrate volume was stripped under reduced pressure. After refrigeration of the filtrate overnight, 8.66 g of the title compound having a purity of greater than 97% was recovered.

The workup was repeated and the filtrate yielded a second crop of title compound (3.87 9) with a purity of greater than 97%.

The filtrate was evaporated in vacuo to remove volatiles, producing a viscous oil. Chromatography of this oil on silica-gel using 20% ethyl acetate in hexane as an eluent provided 3.3 g of the desired product. The overall yield was 82–84%.

EXAMPLE 3

Preparation of Methyl 2-(diphenylphosphino)naphthalene from 2-Bromonaphthalene To a solution of 4.14 g (20 mmol) of 2-bromonaphthalene in 40 ml DMF, was added 0.376 g $NiCl_2(dppe)$ (0.712 mmol). The reaction mixture was cooled to 0° C. and 3.6 ml $ClPPh_2$ (20 mmol) was added dropwise followed by the portionwise addition of 1.74 g zinc (27 mmol) while the internal temperature was kept at 8–14° C. The reaction mixture was heated to 100° C. for 2 hours, at which point 89% conversion of the substrate was observed by gas chromatographic analysis. The reaction was filtered while hot through a short pad of silica gel, and the filtrate was concentrated to one-third volume under reduced pressure. The filtrate was cooled overnight at −10° C. and yielded 3.66 g of the title compound having greater than 97% purity. The volatiles were removed from the filtrate in vacuo to yield an additional 3.2 g of product with the following composition:

Naphthalene 6%
2-Bromonaphthalene 7%
Product 78%
Total yield: 91%.

EXAMPLE 4

Preparation of Benzyldiphenylphosphine from Benzyl Bromide

To a solution of 2.7 ml benzyl bromide (20 mmol) in 40 ml DMF, was added 0.436 g $NiCl_2(dppe)$ (0.826 mmol) The reaction mixture was cooled to 5° C. and 3.6 ml $ClPPh_2$ (20 mmol) was added dropwise followed by the portionwise addition of 1.74 g zinc (27 mmol) while the internal temperature was kept at 8–14° C. The reaction mixture was heated to 83° C. for 45 minutes at which time 81% conversion to the title compound was observed by gas chromatographic analysis.

EXAMPLE 5

Preparation of (S)-BINAP from (S)-1,1'-Binaphth-2,2'-diyl ditriflate

To preactivated zinc powder (1.34 g, 21 mmol), prepared by washing zinc with hydrochloric acid and water and then drying, in 5 ml tetrahydrofuran and a crystal of iodine, was added (S)-1,1'-binaphth-2,2'-diyl ditriflate (3.82 g, 6.9 mmol) in DMF dropwise over 30 minutes at 45° C. The reaction mixture was cooled to room temperature and $NiCl_2$(dppe) (362 mg, 0.68 mmol) was added at once, followed by the dropwise addition of $ClPPh_2$ (2.5 ml, 13.8 mmol) in 8 ml DMF over 15 minutes at 4–7° C., and the mixture was heated with stirring at 100° C. for 19 hours. The reaction was monitored by gas chromatography until starting material was depleted. The dark reddish mixture was filtered while hot. A solid precipitated upon cooling which was collected by filtration and washed with two 5 ml portions of methanol to give 0.54 g of (S)-BINAP.

The filtrate was allowed to stand overnight at 5° C., yielding 0.81 g of crude product. After flash chromatography on a silica gel column, 0.7 g of a white crystalline material (94% purity by gas chromatography) was recovered. This material had a melting point of 41° C., identical to the literature value, and $[\alpha]^D=-210$ (benzene, c=0.1) at 20° C. {literature: $[\alpha]^D=-208$ (benzene, c=0.5) at 20° C.}.

EXAMPLE 6

Preparation of 1-Carbomethoxy-2-(diphenylphosphino)naphthalene

To a solution of 66.6 g (0.195 mol) of 1-carbomethoxy-2-(trifluoromethylsulfonyloxy)naphthalene in 450 ml DMF were added, under a nitrogen atmosphere, 3.65 9 $NiCl_2$(dppe) (6.9 mmol) and 35 ml $ClPPh_2$ (0.195 mol).

The reaction mixture was cooled in an ice-water bath and 15 g zinc (20% excess) was added portionwise at 8–15° C. The mixture was then heated to 108° C. for 2 hours, cooled to 50° C., filtered through silica and washed with three 20 ml portions of methanol. The filtrate was concentrated under vacuum to half of its original volume and allowed to crystallize at 0–4° C. The product was collected and washed with methanol. Further concentration of the filtrate caused additional material to crystallize. The total yield of the title compound was 66.3 g (92%).

EXAMPLE 7

Preparation of 1-Benzylamido-2-(diphenylphosphino)benzene

To a solution of 4.7 g (13 mmol) 2-trifluoromethanesulfonyloxy-N-benzylbenzamide in DMF (50 ml) were added NiCl$_2$(dppe) (0.336 g, 0.64 mmol) and Ph$_2$PCl (2.5 ml, 13.9 mmol) under a nitrogen atmosphere. The reaction mixture was cooled with an ice bath and zinc (0.98 g, 15 mmol) was added portionwise at 5–10° C. The reaction mixture was then heated to 108° C. and monitored by gas chromatography. After 12 hours, a conversion of 73% was observed. The mixture was cooled to room temperature and then filtered through a pad of silica gel. The filtrate was diluted with water (100 ml) and extracted with two 50 ml portions of dichloromethane. Solvent was removed under reduced pressure and the residual paste was crystallized from hot dichloromethane-hexane-methanol to yield 3.74 g (67%) of material in the form of white needles with a melting point of 160° C. The $^1$H NMR and mass spectrum of this material were consistent with the title compound.

EXAMPLE 8

Cross-Coupling of Benzyl Bromide and Ph$_2$PCl in THF

To a solution of benzyl bromide (3.42 g, 20 mmol) in THF (50 ml) was added NiCl$_2$(dppe) (0.275 g, 0.52 mmol). The reaction mixture was cooled with an ice bath and Ph$_2$PCl (3.6 ml, 20 mmol) was added dropwise, followed by portionwise addition of zinc (1.57 g, 24 mmol), while maintaining the reaction temperature in the range between 5 and 9° C. The reaction mixture was then warmed to room temperature and maintained there for 1.25 hours, at which time complete disappearance of starting material and 85% conversion to product were observed by gas chromatography. The mixture was filtered while hot through a pad of silica gel. Removal of solvent under reduced pressure produced an oil, which was diluted with water (50 ml) and extracted with two 20 ml portions of dichloromethane. The organic layers were combined and the solvent was removed under reduced pressure to produce a white residue that was recrystallized from hexane-dichloromethane to give a white crystalline material, found to be the oxide of benzyldiphenylphosphine due to the air sensitivity of the phosphine, in greater than 90% yield.

Other variations and modifications of this invention will be obvious to those skilled in the art. This invention is not limited except as set forth in the claims.

What is claimed is:

1. A method for preparation of a compound of formula

wherein R$^1$ is aryl, alkenyl, cycloalkenyl or aralkyl, any of which may be substituted by one or more of the following: alkyl, aryl, aralkyl, alkoxy, alkanoyl, chloro, fluoro, alkoxycarbonyl, cyano, trifluoromethyl, cycloalkyl or CONR$^4$R$^5$ wherein R$^4$ and R$^5$ are independently hydrogen, alkyl, aryl or aralkyl; R$^2$ and R$^3$ are independently aryl, alkyl, or aralkyl, any of which may be substituted by one or more of the following: alkyl, aryl, aralkyl, alkoxy, alkanoyl, chloro, fluoro, alkoxycarbonyl, cyano, trifluoromethyl, or cycloalkyl; n is 2 where R$^1$ is a difunctional moiety, and n is 1 for any other R$^1$; said method comprising the step of treating a compound of formula R$^1$X$_n$; wherein X is Cl, Br, I, or OSO$_2$Y; wherein Y is alkyl, trihalomethyl, phenyl, halophenyl, or alkylphenyl; with a compound of formula R$^2$R$^3$PCl in the presence of a catalyst and a reductant.

2. The method of claim 1 wherein R$^1$ is phenyl, benzyl, naphthyl, naphthylmethyl, 1,1'-binaphth-2,2'-diyl, pyridyl, pyridylmethyl, furyl, furfuryl, thienyl, thienylmethyl, pyrrolyl, pyrrolylmethyl, phenylene, or xylylene, any of which may be substituted by one or more of the following: alkyl, aryl, aralkyl, alkoxy, alkanoyl, chloro, fluoro, alkoxycarbonyl, cyano, trifluoromethyl, cycloalkyl or CONR$^4$R$^5$ wherein R$^4$ and R$^5$ are independently hydrogen, alkyl, aryl or aralkyl; and R$^2$ and R$^3$ are independently phenyl, alkyl, furyl, thienyl, pyrrolyl, pyridyl, benzyl, or naphthyl, any of which may be substituted by one or more of the following: alkyl, aryl, aralkyl, alkoxy, alkanoyl, chloro, fluoro, alkoxycarbonyl, cyano, trifluoromethyl, cycloalkyl, or CONR$^4$R$^5$ wherein R$^4$ and R$^5$ are independently hydrogen, alkyl, aryl or aralkyl; n is 2 where R$^1$ is 1,1'-binaphth-2,2'-diyl, phenylene, or xylylene, and n is 1 for any other R$^1$.

3. The method of claim 2 wherein the catalyst is a nickel compound.

4. The method of claim 2, wherein R$^2$ and R$^3$ are each phenyl.

5. The method of claim 4, wherein R$^1$ is 1,1'-binaphth-2,2'-diyl.

6. The method of claim 5, wherein R$^1$ is (R)-1,1'-binaphth-2,2'-diyl.

7. The method of claim 5, wherein R$^1$ is (S)-1,1'-binaphth-2,2'-diyl.

8. The method of claim 5, wherein X is OSO$_2$Y and Y is trifluoromethyl.

9. The method of claim 5, wherein X is Br.

10. The method of claim 4, wherein R$^1$ is 1-carboxymethy-2-naphthyl.

11. The method of claim 10, wherein X is OSO$_2$Y and Y is trifluoromethyl.

* * * * *